(12) United States Patent
Liu et al.

(10) Patent No.: US 9,399,243 B1
(45) Date of Patent: Jul. 26, 2016

(54) METHOD OF PREPARING CARBON-COATED CUPROUS OXIDE

(71) Applicant: Jianhong Liu, Shenzhen (CN)

(72) Inventors: Jianhong Liu, Shenzhen (CN); Qianling Zhang, Shenzhen (CN); Chuanxin He, Shenzhen (CN); Jian Xu, Shenzhen (CN); Xiaoming Li, Shenzhen (CN); Chuhong Liao, Shenzhen (CN); Xiangning Ren, Shenzhen (CN)

(73) Assignee: SHENZHEN EIGEN-EQUATION GRAPHENE TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 14/821,782

(22) Filed: Aug. 9, 2015

(51) Int. Cl.
| | |
|---|---|
| A01B 1/00 | (2006.01) |
| B01J 27/20 | (2006.01) |
| B01J 23/72 | (2006.01) |
| B01J 23/835 | (2006.01) |
| B05D 7/00 | (2006.01) |
| B05D 3/04 | (2006.01) |
| B05D 3/02 | (2006.01) |
| A01N 25/26 | (2006.01) |
| A01N 59/20 | (2006.01) |
| B01J 37/08 | (2006.01) |
| B01J 37/02 | (2006.01) |
| B01J 35/02 | (2006.01) |

(52) U.S. Cl.
CPC ........ B05D 7/00 (2013.01); A01N 25/26 (2013.01); A01N 59/20 (2013.01); B01J 23/72 (2013.01); B01J 23/835 (2013.01); B01J 27/20 (2013.01); B01J 35/026 (2013.01); B01J 37/0221 (2013.01); B01J 37/0236 (2013.01); B01J 37/084 (2013.01); B05D 3/0272 (2013.01); B05D 3/0466 (2013.01)

(58) Field of Classification Search
None
See application file for complete search history.

(56) References Cited

U.S. PATENT DOCUMENTS

| | | | | |
|---|---|---|---|---|
| 5,081,097 A | * | 1/1992 | Sharma | B01J 20/20 423/219 |
| 6,384,128 B1 | * | 5/2002 | Wadahara | C08K 7/02 524/496 |
| 8,741,243 B2 | * | 6/2014 | Gadkaree | 423/210 |
| 8,945,501 B2 | * | 2/2015 | Liu | B82Y 30/00 252/502 |
| 2005/0025974 A1 | * | 2/2005 | Lennhoff | B82Y 30/00 428/408 |
| 2011/0281027 A1 | * | 11/2011 | Vogt | C23C 18/08 427/226 |
| 2013/0116350 A1 | * | 5/2013 | Abbaslou | B01J 23/8872 518/713 |
| 2013/0131418 A1 | * | 5/2013 | Liu | C07C 5/3332 585/661 |
| 2015/0018201 A1 | * | 1/2015 | Hoekstra | B01K 21/185 502/185 |

* cited by examiner

Primary Examiner — Guinever S Gregorio
(74) Attorney, Agent, or Firm — Matthias Scholl P.C.; Matthias Scholl

(57) ABSTRACT

A method of preparing carbon-coated cuprous oxide, including: (1) preparing a liquid polyacrylonitrile (LPAN) solution, stirring the LPAN solution to yield a cyclized polyacrylonitrile solution; (2) heating the cyclized LPAN solution to yield a thermally-oxidized polyacrylonitrile (OPAN); (3) mixing the thermally-oxidized polyacrylonitrile with a copper compound to yield a mixture, and adding to the mixture a hydrophilic solvent or a hydrophobic solvent, thus yielding a polyacrylonitrile coated copper compound; (4) drying the polyacrylonitrile coated copper compound in an oven until the solvent is evaporated completely and the polyacrylonitrile coated on the copper compound is crosslinked to form a solid, where yielding a carbonized precursor coated copper compound; and (5) calcining the carbonized precursor coated copper compound in the presence of an inert gas flow of between 10 and 500 mL/min.

15 Claims, 5 Drawing Sheets

METHOD OF PREPARING CARBON-COATED CUPROUS OXIDE

BACKGROUND OF THE INVENTION

1. Field of the Invention

The invention relates to a method of preparing carbon-coated cuprous oxide.

2. Description of the Related Art

Conventional methods for preparing cuprous oxide are relatively complex, low in yield, and high in cost.

SUMMARY OF THE INVENTION

In view of the above-described problems, it is one objective of the invention to provide a method of preparing carbon-coated cuprous oxide that features simple process, low production cost and high yield.

To achieve the above objective, in accordance with one embodiment of the invention, there is provided a method of preparing carbon-coated cuprous oxide, the method comprising:

(1) preparing a liquid polyacrylonitrile (LPAN) solution as a carbon source, stirring the LPAN solution at between 100 and 200° C. for between 100 and 200 hrs to yield a cyclized polyacrylonitrile solution;

(2) heating the cyclized LPAN solution at between 200 and 300° C. for between 1 and 10 hrs to yield a thermally-oxidized polyacrylonitrile (OPAN) comprising a ladder structure;

(3) mixing the thermally-oxidized polyacrylonitrile with a copper compound with a mass ratio thereof being between 0.1:1 and 0.9:1, to yield a mixture, and adding to the mixture a hydrophilic solvent or a hydrophobic solvent with a mass ratio of the mixture to the solvent being between 0.1:1 and 0.5:1, to yield a polyacrylonitrile coated copper compound;

(4) drying the polyacrylonitrile coated copper compound in an oven at a temperature of between 200 and 250° C. for between 1 and 10 hrs until the solvent is evaporated completely and the polyacrylonitrile coated on the copper compound is crosslinked to form a solid, to yield a carbonized precursor coated copper compound; and (5) calcining the carbonized precursor coated copper compound in the presence of an inert gas flow of between 10 and 500 mL/min for between 1 and 10 hrs at a temperature of between 250 and 500° C., to yield a carbon-coated cuprous oxide.

In a class of this embodiment, in 1), a dopant is added to and uniformly mixed with the cyclized LPAN solution.

In a class of this embodiment, the LPAN has a relative molecular weight of between 106 and 100000; the PLAN is a homopolymer of acrylonitrile, or a copolymer of acrylonitrile and a vinyl monomer, and the vinyl monomer is selected from the group of styrene, methyl methacrylate, hydroxyethyl methylacrylate, acrylic acid, itaconic acid.

In a class of this embodiment, the relative molecular weight of the LPAN is between 1600 and 25000.

In a class of this embodiment, a mass ratio of the dopant to the LPAN is between 0.01:1 and 0.5:1, and the mixing is achieved by stirring, ultrasound, or ball milling.

In a class of this embodiment, the dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, or a mixture thereof; and the non-metallic dopant is silicon, phosphorus, boron, nitrogen, carbon, sulfur, or a compound thereof, or a mixture thereof.

In a class of this embodiment, the inert gas is nitrogen or argon.

Advantages of the method of preparing carbon-coated cuprous oxide are summarized as follows. The obtained carbon-coated cuprous oxide has good compatibility with resins and the carbon membrane is porous, so that the release speed of cuprous oxide can be effectively controlled, which is favorable for the carbon-coated cuprous oxide to be used as an antifouling additive for marine antifouling paints. In addition, cuprous oxide is a catalyst capable of responding to visible light, the outer coating of polyacrylonitrile thereof can prevent the oxidation of cuprous oxide, and the cuprous oxide can be slowly released to the surface of the coating via the porous coating, thereby increasing the contact area of the adsorbate and catalyst, and improving the catalytic performance. In the future, cuprous oxide is expected to replace titanium dioxide to become the most widely-used photocatalyst. The method of the invention involves a simple process and low production costs, and the resulting carbon-coated cuprous oxide has high purity, high yield, uniform distribution of particle sizes, and good morphology. The liquid LPAN solution contains multiple functional groups, and as a liquid precursor, after being modified using a dopant, the liquid LPAN can uniformly mix with and bind to the dopant.

BRIEF DESCRIPTION OF THE DRAWINGS

The invention is described hereinbelow with reference to the accompanying drawings, in which.

DETAILED DESCRIPTION OF THE EMBODIMENTS

Figure 1:
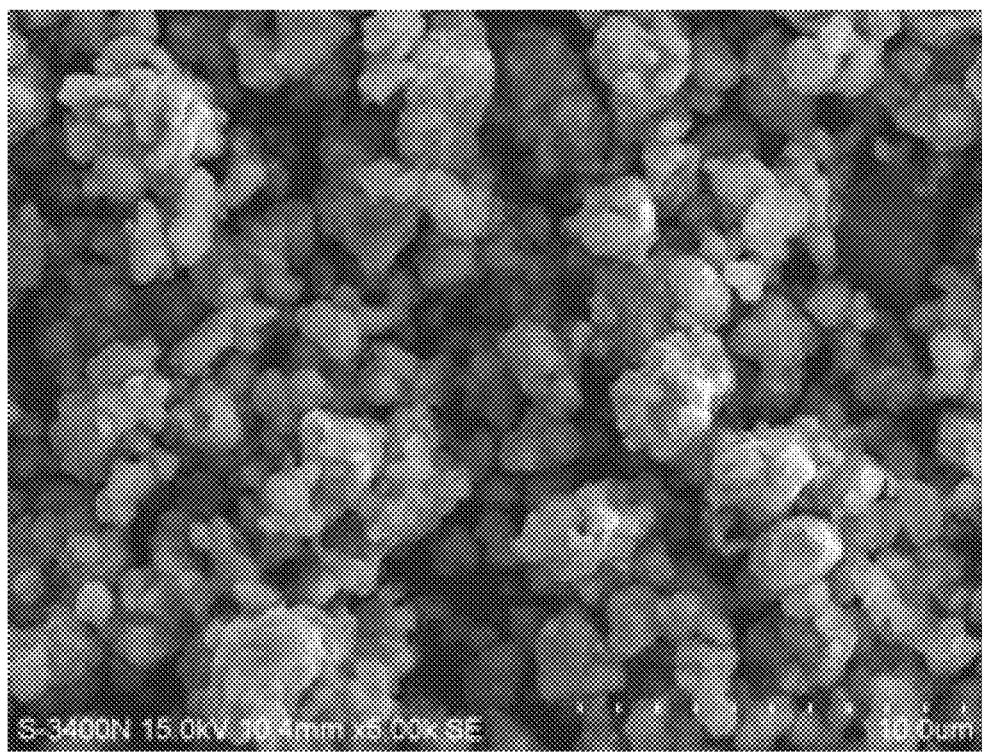
FIG. 1 is a SEM pattern of a product prepared in Example 1, where the product is carbon-coated cuprous oxide and a small amount of carbon-coated copper.

For further illustrating the invention, experiments detailing a method of preparing a carbon-coated cuprous oxide are described below. It should be noted that the following examples are intended to describe and not to limit the invention.

The invention provides a method of preparing a carbon-coated cuprous oxide, the method comprising:

(1) Preparing a self-made liquid polyacrylonitrile (LPAN) solution as a carbon source, stirring the LPAN solution at between 100 and 200° C. for between 100 and 200 hrs to yield a cyclized polyacrylonitrile solution.

The invention employs the self-made PLAN instead of dilute PLAN as a carbon source, and the former presents a liquid in the temperature of between minus 80° C. and 200° C., with a concentration of 0.8 and 1.2 g/cm$^2$. The polymer is a long chain macromolecule with high molecular weight and high carbon content, and thus provides a structure base for the carbon coating.

(2) Heating the cyclized LPAN solution at between 200 and 300° C. for between 1 and 10 hrs to yield a thermally-oxidized polyacrylonitrile (OPAN) comprising a ladder structure. The total content of the self-made PLAN is between 10-100 kg, which has stable chemical properties and can stored stably for a long time after being heated at the temperature of 200-300° C. For each thermal oxidation, the usage amount is 50-400 g.

(3) Mixing the thermally-oxidized polyacrylonitrile with a copper compound (comprising copper oxide and a copper salt) with a mass ratio thereof being between 0.1:1 and 0.9:1, to yield a mixture, and adding to the mixture a hydrophilic solvent or a hydrophobic solvent with a mass ratio of the mixture to the solvent being between 0.1:1 and 0.5:1, to yield a polyacrylonitrile coated copper compound;

(4) Drying the polyacrylonitrile coated copper compound in an oven at a temperature of between 200 and 250° C. for between 1 and 10 hrs until the solvent is evaporated completely and the polyacrylonitrile coated on the copper compound is crosslinked to form a solid, to yield a carbonized precursor coated copper compound; and (5) Calcining the carbonized precursor coated copper compound in the presence of an argon or nitrogen gas flow of between 10 and 500 mL/min for between 1 and 10 hrs at a temperature of between 250 and 500° C., to yield a carbon-coated cuprous oxide.

As an improvement, in 1), a dopant, for example, copper, is added to and uniformly mixed with the cyclized LPAN solution.

As an improvement, the carbon source is polypyrrole, polythiophene, polyaniline, polyacetylene, polystyrene, polycarbonate, or polyamide resin instead of PLAN. The relative molecular weight of the LPAN is between 1600 and 25000. The LPAN is a carbon source PLAN. The carbon source is a homopolyer of the polymer (that is, the LPAN is a homopolymer of acrylonitrile), or a copolymer of acrylonitrile and a vinyl monomer, and the vinyl monomer is selected from the group of styrene, methyl methacrylate, hydroxyethyl methylacrylate, acrylic acid, itaconic acid. The mass ratio of the dopant to the LPAN is between 0.01:1 and 0.5:1, and the mixing is achieved by stirring, ultrasound, or ball milling.

The dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, or a mixture thereof; and the non-metallic dopant is silicon, phosphorus, boron, nitrogen, carbon, sulfur, or a compound thereof, or a mixture thereof; the inert gas is nitrogen or argon.

Specifically, the relative molecular weight of the LPAN is between 1600 and 25000.

In 2), the cyclized LPAN solution is heated at between 200 and 300° C. for between 1 and 10 hrs to yield the thermally-oxidized polyacrylonitrile (OPAN) comprising a ladder structure. The OPAN has high carbon content and stable structure, thus provides a structure base for the carbonization and crosslinking.

As an improvement, in 1), a dopant is added to and uniformly mixed with the cyclized LPAN solution, and the mixing is achieved by stirring, ultrasound, or ball milling. The cyclized LPAN solution has multiple functional groups, which are adapted to tightly bind to the dopant or carbon material. Part of LPAN functional groups can coordinate with the dopant to achieve compatibility and coating in the molecular level. After grinding or stirring, the LPAN and the dopant are fully mixed and contacted.

Preferably, in 3), a sieve having a mesh of 200-400 mesh is involved.

The obtained carbon-coated cuprous oxide has good compatibility with resins and the carbon membrane is porous, so that the release speed of cuprous oxide can be effectively controlled, which is favorable for the carbon-coated cuprous oxide to be used as an antifouling additive for marine antifouling paints. In addition, cuprous oxide is a catalyst capable of responding to visible light, the outer coating of polyacrylonitrile thereof can prevent the oxidation of cuprous oxide, and the cuprous oxide can be slowly released to the surface of the coating via the porous coating, thereby increasing the contact area of the adsorbate and catalyst, and improving the catalytic performance. In the future, cuprous oxide is expected to replace titanium dioxide to become the most widely-used photocatalyst. The method of the invention involves a simple process and low production costs, and the resulting carbon-coated cuprous oxide has high purity, high yield, uniform distribution of particle sizes, and good morphology. The liquid LPAN solution contains multiple functional groups, and as a liquid precursor, after being modified using a dopant, the liquid LPAN can uniformly mix with and bind to the dopant.

Example 1

Figure 2:
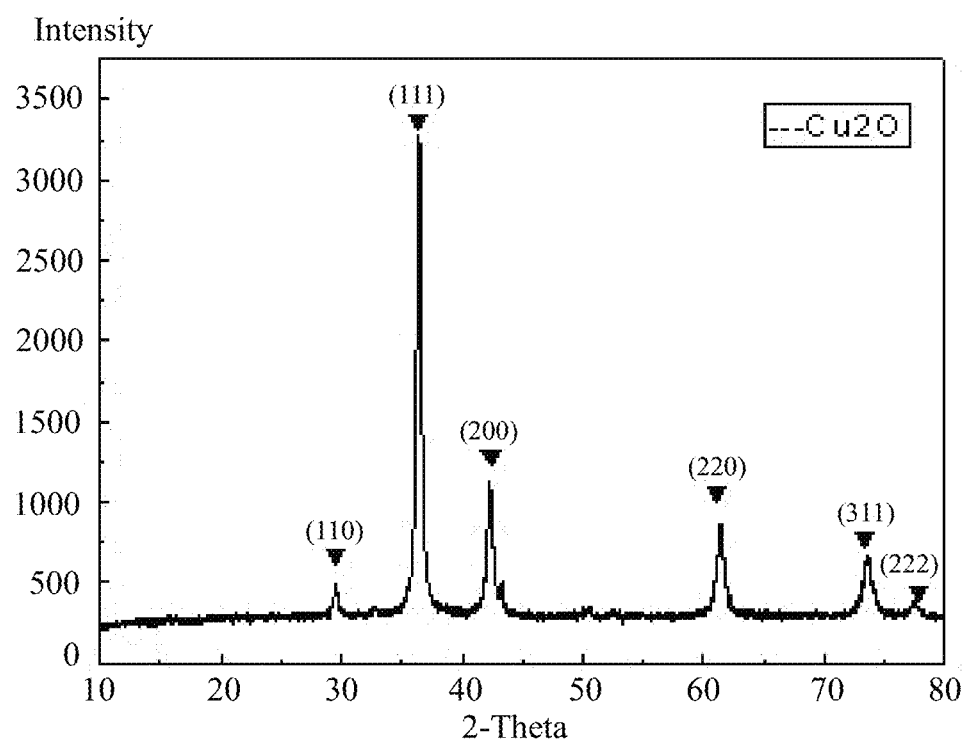
FIG. 2 is an XRD pattern of a product prepared in Example 1, where the product is carbon-coated cuprous oxide and a small amount of carbon-coated copper.
Figure 3:
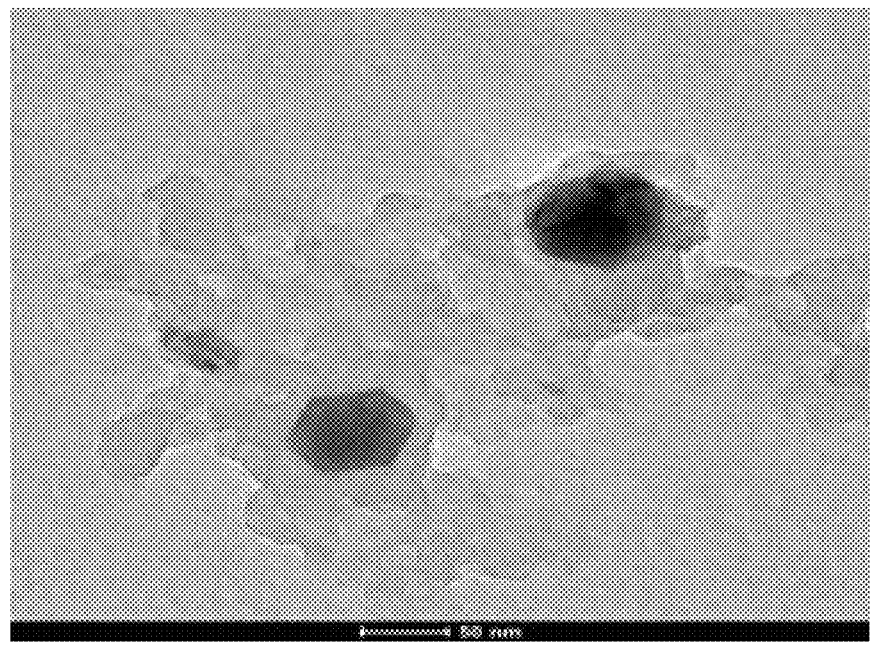
FIG. 3 is a TEM pattern of a product prepared in Example 1, where the product is carbon-coated cuprous oxide and a small amount of carbon-coated copper.

2 g of self-made liquid polyacrylonitrile (LPAN) solution (molecular weight 4000) was stirred at 120° C. for 120 hrs, to yield a cyclized polyacrylonitrile solution. The cyclized LPAN solution was heated at between 200 and 300° C. for 8 hrs to yield a thermally-oxidized polyacrylonitrile (OPAN) comprising a ladder structure. The thermally-oxidized polyacrylonitrile was mixed with 11.25 g of copper oxide and 15-30 mL of a solvent. The resulting mixture was ball milled using a planetary type ball mill for 10 hrs (400 rad/min), and the ratio of grinding media to material was 15:1. Thereafter, a product was collected and dried in an oven at 220° C. for 3 hrs, to yield a thermally-oxidized precursor. The thermally-oxidized precursor was calcined in a ceramic boat in the presence of an inert gas flow of 150 mL/min for 4 hrs at the temperature of 350° C., and then was cooled to room temperature, to yield a mixture of carbon-coated copper and carbon-coated cuprous oxide, the structures thereof are shown in FIGS. 1-3.

Example 2

Figure 4:
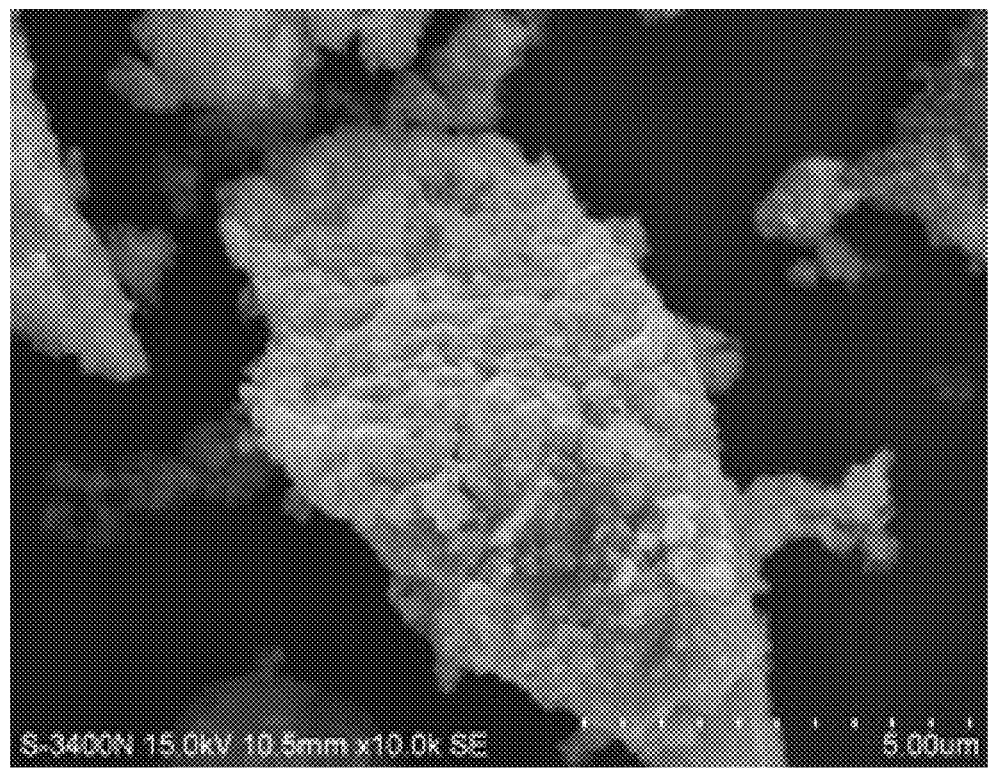
FIG. 4 is a SEM pattern of a product prepared in Example 2, where the product is carbon-coated cuprous oxide and a small amount of carbon-coated copper.
Figure 5:
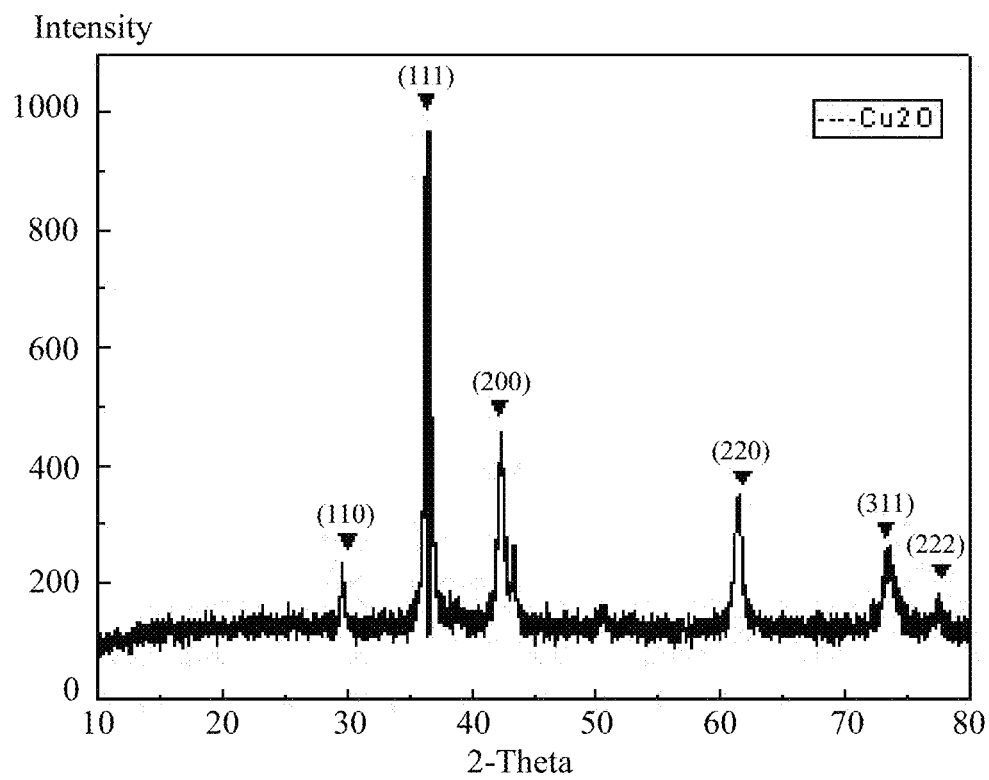
FIG. 5 is an XRD pattern of a product prepared in Example 2, where the product is carbon-coated cuprous oxide and a small amount of carbon-coated copper.

4 g of polypyrrole (molecular weight 4000) was stirred at 120° C. for 120 hrs, to yield a cyclized solution. The cyclized solution was heated at between 200 and 300° C. for 8 hrs to yield a thermally-oxidized polypyrrole solid comprising a ladder structure. The thermally-oxidized polypyrrole solid was mixed with 10 g of copper oxide and 15-30 mL of a solvent. The resulting mixture was ball milled using a planetary type ball mill for 8 hrs (400 rad/min), and the ratio of grinding media to material was 15:1. Thereafter, a product was collected and dried in an oven at 220° C. for 3 hrs, to yield a thermally-oxidized precursor. The thermally-oxidized precursor was calcined in a ceramic boat in the presence of an inert gas flow of 150 mL/min for 4 hrs at the temperature of 300° C., and then was cooled to room temperature, to yield a mixture of carbon-coated cuprous oxide (a small amount) and carbon-coated copper oxide, the structures thereof are shown in FIGS. 4-5.

Example 3

Figure 6:
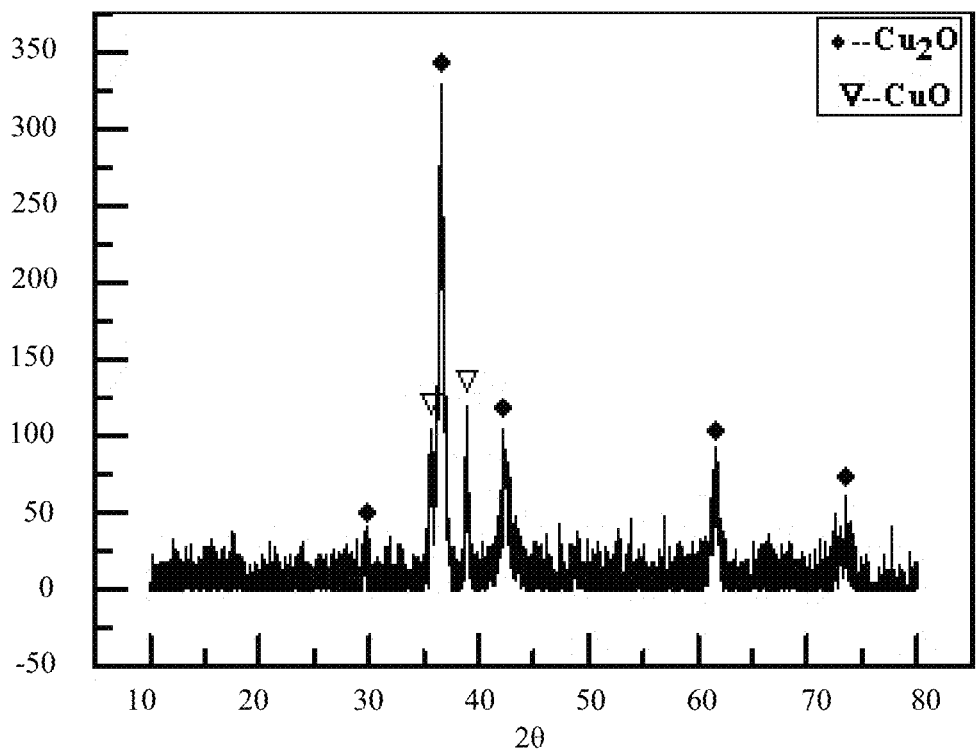
FIG. 6 is an XRD pattern of a product prepared in Example 3, where the product is carbon-coated cuprous oxide and a small amount of carbon-coated copper oxide.
Figure 7:
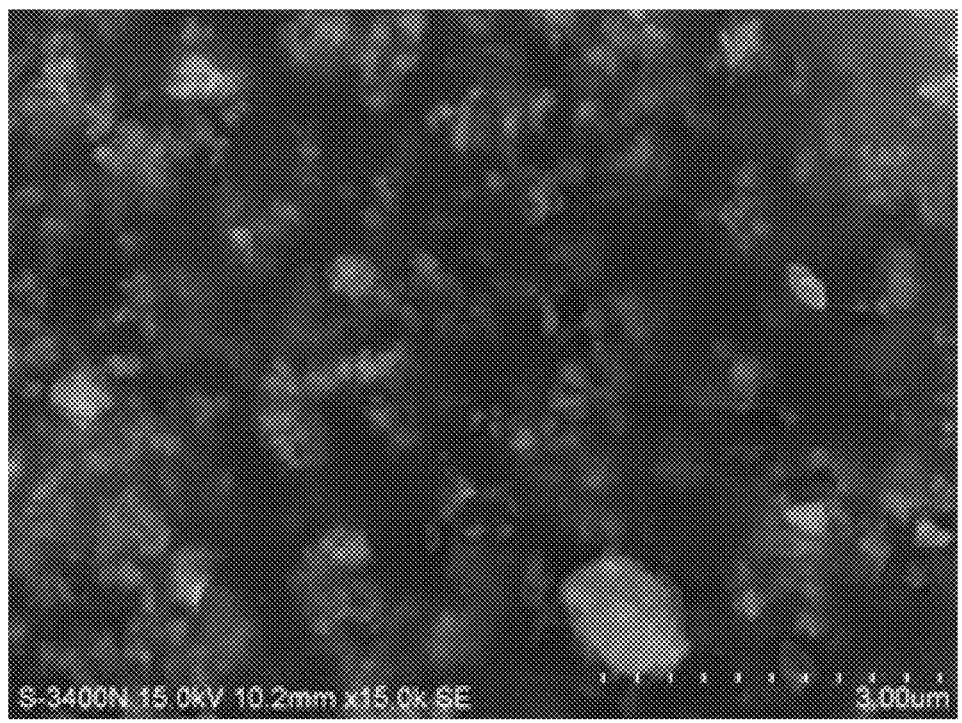
FIG. 7 is a TEM pattern of a product prepared in Example 3, where the product is carbon-coated cuprous oxide and a small amount of carbon-coated copper oxide.

2 g of polythiophene (molecular weight 4000) was stirred at 120° C. for 120 hrs, to yield a cyclized polythiophene solution. The cyclized polythiophene solution was heated at between 200 and 300° C. for 8 hrs to yield a thermally-oxidized polythiophene (OPTh) comprising a ladder structure. The thermally-oxidized polyacrylonitrile was mixed with 6.25 g of copper oxide and 15-30 mL of deionized water as a solvent. The resulting mixture was ball milled using a planetary type ball mill for 10 hrs (400 rad/min), and the ratio of grinding media to material was 15:1. Thereafter, a product was collected and dried in an oven at 220° C. for 3 hrs, to yield a thermally-oxidized precursor. The thermally-oxidized precursor was calcined in a ceramic boat in the presence of an inert gas flow of 150 mL/min for 4 hrs at the temperature of 250° C., and then was cooled to room temperature, to yield a mixture of carbon-coated cuprous oxide and carbon-coated copper oxide (a small amount), the structures thereof are shown in FIGS. 6-7.

Example 4

Figure 8:
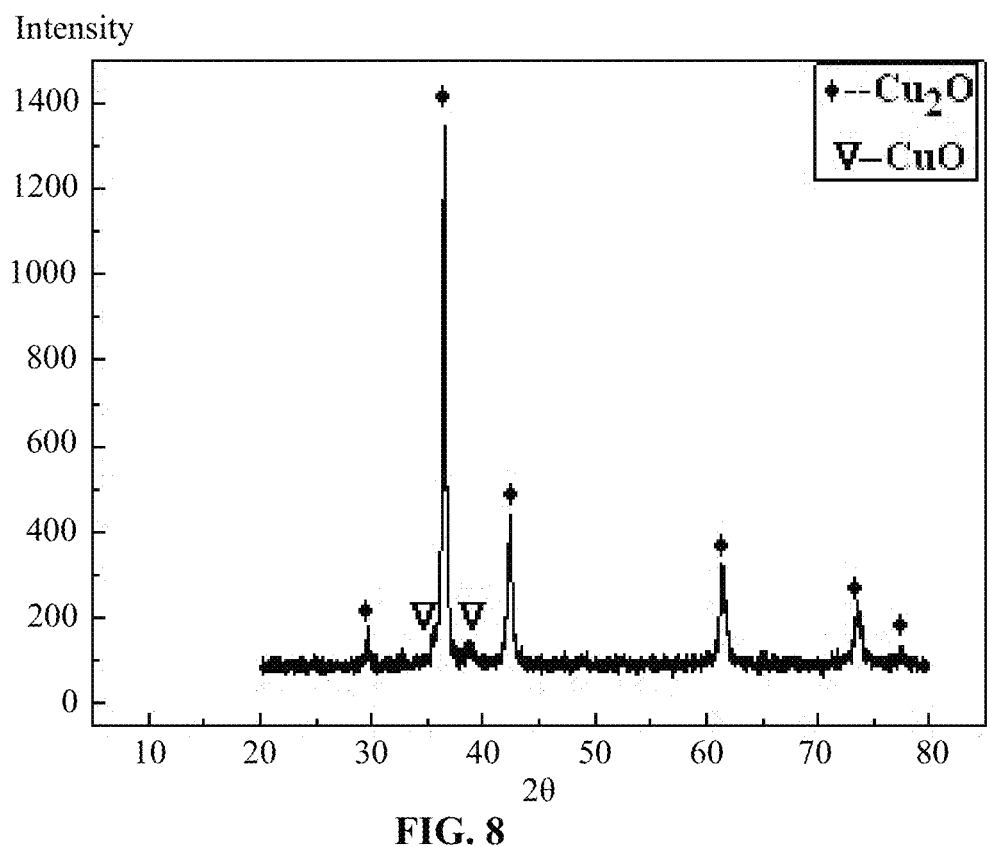
FIG. 8 is an XRD pattern of a product prepared in Example 4, where the product is carbon-coated cuprous oxide and a small amount of carbon-coated copper oxide.
Figure 9:
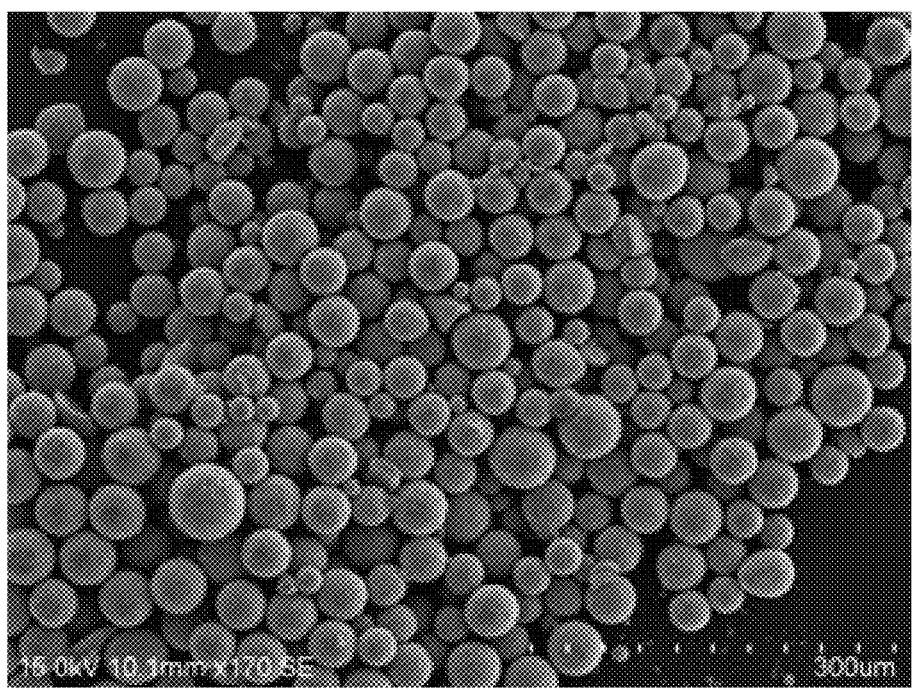
FIG. 9 is a TEM pattern of a product prepared in Example 4, where the product is carbon-coated cuprous oxide and a small amount of carbon-coated copper oxide.
Figure 10:
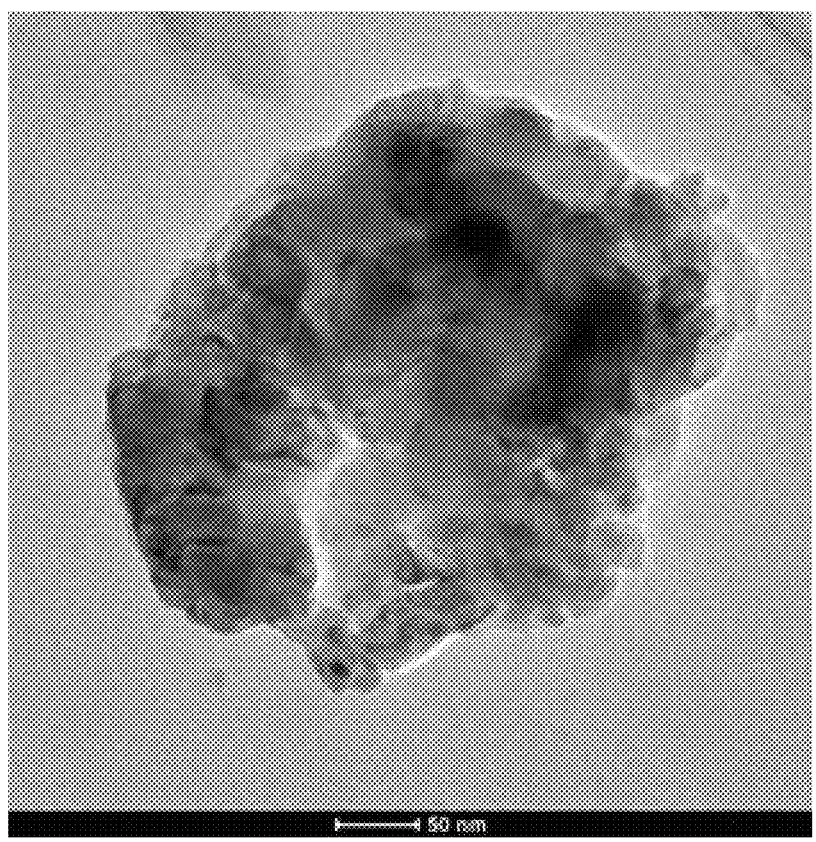
FIG. 10 is a SEM pattern of a product prepared in Example 4, where the product is carbon-coated cuprous oxide and a small amount of carbon-coated copper oxide.

2 g of polyacrylonitrile solution (molecular weight 4000) was stirred at 120° C. for 120 hrs, to yield a cyclized polyacrylonitrile solution. The cyclized LPAN solution was heated at between 200 and 300° C. for 8 hrs to yield a thermally-oxidized polyacrylonitrile (OPAN) comprising a ladder structure. The thermally-oxidized polyacrylonitrile was mixed with 562.5 g of copper oxide and 500 mL water as a solvent. The resulting mixture was ball milled using a nano attrition mill for 5 hrs (400 rad/min), and the ratio of grinding media to material was 15:1. Thereafter, a product was collected and dried by spray, to yield a thermally-oxidized precursor. The thermally-oxidized precursor was calcined in a mullite ceramic boat in the presence of an inert gas flow of 500 mL/min for 10 hrs at the temperature of 285° C., and then was cooled to room temperature, to yield a mixture of carbon-coated cuprous oxide and carbon-coated copper oxide (a small amount), the structures thereof are shown in FIGS. 8-10.

The obtained carbon-coated cuprous oxide has good compatibility with resins and the carbon membrane is porous, so that the release speed of cuprous oxide can be effectively controlled, which is favorable for the carbon-coated cuprous oxide to be used as an antifouling additive for marine antifouling paints. In addition, cuprous oxide is a catalyst capable of responding to visible light, the outer coating of polyacrylonitrile thereof can prevent the oxidation of cuprous oxide, and the cuprous oxide can be slowly released to the surface of the coating via the porous coating, thereby increasing the contact area of the adsorbate and catalyst, and improving the catalytic performance. In the future, cuprous oxide is expected to replace titanium dioxide to become the most widely-used photocatalyst. The method of the invention involves a simple process and low production costs, and the resulting carbon-coated cuprous oxide has high purity, high yield, uniform distribution of particle sizes, and good morphology. The liquid LPAN solution contains multiple functional groups, and as a liquid precursor, after being modified using a dopant, the liquid LPAN can uniformly mix with and bind to the dopant.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A method of preparing carbon-coated cuprous oxide, the method comprising:
 (1) preparing a liquid polyacrylonitrile (LPAN) solution as a carbon source, stirring the LPAN solution at between 100 and 200° C. for between 100 and 200 hrs to yield a cyclized polyacrylonitrile solution;
 (2) heating the cyclized LPAN solution at between 200 and 300° C. for between 1 and 10 hrs to yield a thermally-oxidized polyacrylonitrile (OPAN) comprising a ladder structure;
 (3) mixing the thermally-oxidized polyacrylonitrile with a copper compound with a mass ratio thereof being between 0.1:1 and 0.9:1, to yield a mixture, and adding to the mixture a hydrophilic solvent or a hydrophobic solvent with a mass ratio of the mixture to the solvent being between 0.1:1 and 0.5:1, to yield a polyacrylonitrile coated copper compound;
 (4) drying the polyacrylonitrile coated copper compound in an oven at a temperature of between 200 and 250° C. for between 1 and 10 hrs until the solvent is evaporated completely and the polyacrylonitrile coated on the copper compound is crosslinked to form a solid, to yield a carbonized precursor coated copper compound; and
 (5) calcining the carbonized precursor coated copper compound in the presence of an inert gas flow of between 10 and 500 mL/min for between 1 and 10 hrs at a temperature of between 250 and 500° C., to yield a carbon-coated cuprous oxide.

2. The method of claim 1, wherein in 1), a dopant is added to and uniformly mixed with the cyclized LPAN solution.

3. The method of claim 2, wherein a mass ratio of the dopant to the LPAN is between 0.01:1 and 0.5:1, and the mixing is achieved by stirring, ultrasound, or ball milling.

4. The method of claim 2, wherein the dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, or a mixture thereof; and the non-metallic dopant is silicon, phosphorus, boron, nitrogen, carbon, sulfur, or a compound thereof, or a mixture thereof.

5. The method of claim 1, wherein the LPAN has a relative molecular weight of between 106 and 100000; the PLAN is a homopolymer of acrylonitrile, or a copolymer of acrylonitrile and a vinyl monomer, and the vinyl monomer is selected from the group of styrene, methyl methacrylate, hydroxyethyl methylacrylate, acrylic acid, itaconic acid.

6. The method of claim 5, wherein the relative molecular weight of the LPAN is between 1600 and 25000.

7. The method of claim 1, wherein the inert gas is nitrogen or argon.

8. The method of claim 1, wherein the PLAN is self-made and presents a liquid in a temperature of between minus 80° C. and 200° C., with a concentration of 0.8 and 1.2 g/cm$^2$.

9. The method of claim 8, wherein the copper compound is a mixture of copper oxide and a copper salt; the LPAN has a relative molecular weight of between 106 and 100000; the PLAN is a homopolymer of acrylonitrile, or a copolymer of acrylonitrile and a vinyl monomer, and the vinyl monomer is selected from the group of styrene, methyl methacrylate, hydroxyethyl methylacrylate, acrylic acid, itaconic acid.

10. The method of claim 9, wherein in 2), a dopant is added to and uniformly mixed with the cyclized LPAN solution prior to the heating, a mass ratio of the dopant to the LPAN is between 0.01:1 and 0.5:1, and the mixing is achieved by stirring, ultrasound, or ball milling; the dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, or a mixture thereof; and the non-metallic dopant is silicon, phosphorus, boron, nitrogen, carbon, sulfur, or a compound thereof, or a mixture thereof; the inert gas is nitrogen or argon.

11. The method of claim 9, wherein the relative molecular weight of the LPAN is between 1600 and 25000.

12. The method of claim 9, wherein the dopant is tin powder.

13. The method of claim 1, wherein the carbon source is polypyrrole, polythiophene, polyaniline, polyacetylene, polystyrene, polycarbonate, or polyamide resin instead of PLAN.

14. The method of claim 13, wherein in 2), a dopant is added to and uniformly mixed with the carbon source prior to the heating, a mass ratio of the dopant to the carbon source is between 0.01:1 and 0.5:1, and the mixing is achieved by stirring, ultrasound, or ball milling; the dopant is a metallic dopant or a non-metallic dopant; the metallic dopant is a pure metal comprising tin, copper, silver, aluminum, chromium, iron, manganese, titanium, nickel, and cobalt, or a metal oxide, metal nitride, metal boride, metal fluoride, metal bromide, metal sulfide, or a mixture thereof; and the non-metallic dopant is silicon, phosphorus, boron, nitrogen, carbon, sulfur, or a compound thereof, or a mixture thereof; the inert gas is nitrogen or argon.

15. The method of claim 14, wherein the dopant is tin powder.

* * * * *